United States Patent
Tsuang et al.

(10) Patent No.: US 8,062,372 B2
(45) Date of Patent: Nov. 22, 2011

(54) SPINAL FUSION DEVICE

(75) Inventors: Yang-Hwei Tsuang, Taipei (TW);
Jui-Sheng Sun, Taipei (TW); Chun-Jen Liao, Taipei (TW); Chen-Chi Tsai, Taipei County (TW); Shan-Chang Chueh, Taipei (TW); Yi-Hung Lin, Hsinchu County (TW); Shian-Yih Wang, Taipei (TW); I-Fan Chiu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 556 days.

(21) Appl. No.: 11/611,821

(22) Filed: Dec. 15, 2006

(65) Prior Publication Data
US 2007/0156240 A1 Jul. 5, 2007

Related U.S. Application Data

(60) Provisional application No. 60/755,121, filed on Dec. 29, 2005.

(51) Int. Cl.
*A61F 2/44* (2006.01)

(52) U.S. Cl. .................. 623/17.16; 623/17.11

(58) Field of Classification Search ............. 623/17.11, 623/17.16, 17.12, 17.13–17.15
See application file for complete search history.

(56) References Cited

U.S. PATENT DOCUMENTS

| | | | |
|---|---|---|---|
| 5,433,718 A * | 7/1995 | Brinker | 606/62 |
| 5,609,635 A | 3/1997 | Michelson | |
| 5,865,848 A | 2/1999 | Baker | |
| 6,245,108 B1 | 6/2001 | Biscup | |
| 6,296,665 B1 * | 10/2001 | Strnad et al. | 623/17.16 |
| 6,379,385 B1 * | 4/2002 | Kalas et al. | 623/17.11 |
| 6,743,256 B2 | 6/2004 | Mason | |
| 6,761,738 B1 * | 7/2004 | Boyd | 623/17.11 |
| 6,942,698 B1 | 9/2005 | Jackson | |
| 6,979,353 B2 * | 12/2005 | Bresina | 623/17.16 |
| 7,641,690 B2 * | 1/2010 | Abdou | 623/17.11 |
| 2001/0014826 A1 * | 8/2001 | Biedermann et al. | 623/17.11 |
| 2002/0151976 A1 * | 10/2002 | Foley et al. | 623/17.11 |
| 2003/0195629 A1 * | 10/2003 | Pafford et al. | 623/17.16 |
| 2004/0122518 A1 * | 6/2004 | Rhoda | 623/17.11 |
| 2004/0199251 A1 * | 10/2004 | McCombe et al. | 623/17.11 |
| 2005/0021144 A1 * | 1/2005 | Malberg et al. | 623/17.11 |
| 2005/0085914 A1 * | 4/2005 | Lange et al. | 623/17.11 |
| 2005/0251257 A1 * | 11/2005 | Mitchell et al. | 623/17.11 |

FOREIGN PATENT DOCUMENTS

| | | |
|---|---|---|
| CN | 1122686 | 5/1996 |
| JP | 8266563 | 10/1996 |
| TW | 519488 | 2/2003 |
| TW | 233347 B | 6/2005 |
| WO | WO 2005/037137 A2 | 4/2005 |

* cited by examiner

*Primary Examiner* — Thomas C. Barrett
*Assistant Examiner* — Michael T Schaper

(57) ABSTRACT

A spinal fusion device abutting and fixed between adjacent vertebrae. The spinal fusion device includes a support frame. The support frame has a plurality of extending bodies, each radially extending from a center of the support frame. A predetermined gap exists between every two adjacent extending bodies, receiving a bone graft.

25 Claims, 4 Drawing Sheets

SPINAL FUSION DEVICE

BACKGROUND OF THE INVENTION

1. Field of the Invention

The present invention relates to spinal fusion, and in particular to a device enhancing bone fusion.

2. Description of the Related Art

When the human spinal column is subjected to force or extreme angles, discs between adjacent vertebrae can experience long-term compression, whereby soft tissues of the discs retrograde or protrude from the spinal column. The protruded soft tissues of the disc press nerves, causing pain.

To solve the aforementioned problem, the disc is conventionally removed. A bone graft is then implanted in the gap vacated by the disc, fusing the adjacent vertebrae. The spinal column is thus fixed and stabilized. Moreover, to guarantee bone fusion and prevent the bone graft from breakage and separation from the vertebrae due to insufficient strength thereof, an internal cage is often applied with the bone graft. In order to bear high compression or stress from the vertebrae in different positions, the internal cage is often metal (such as stainless steel or titanium alloy) or macromolecular material (such as Polyetheretherketone, PEEK).

In addition to supporting the adjacent vertebrae, the internal cage guides newgrown bone proliferating from adjacent vertebrae thereinto, thereby enabling bone fusion. Specifically, the internal cage has a hollow interior to receive the bone graft, which induces the bone fusion. Additionally, to reduce complexity of surgery and hospital time, the internal cage combines artificial porous bone material to induce proliferation of bone.

U.S. Pat. No. 6,245,108 discloses a prosthetic implant comprising a hollow casing with a plurality of ridges formed thereon. The ridges enhance engagement between the prosthetic implant and adjacent vertebrae, such that the prosthetic implant can be secured therebetween. The hollow casing receives a bone graft. Nevertheless, fragments of the bone graft easily pass out of the hollow casing, increasing the difficulty of implantation.

U.S. Pat. No. 5,609,635 discloses an interbody spinal fusion implant configured with an upper plate and a lower plate. A bone graft is contained in the interbody spinal fusion implant and maintained between the upper plate and the lower plate, preventing fragments from escaping during implantation surgery.

U.S. Pat. No. 5,865,848 discloses a spinal fusion implant assembly with a detachable structure receiving a bone graft. Multiple complementary protrusions and recesses are formed on a-top surface and a bottom surface, enhancing engagement between the spinal fusion implant assembly and adjacent vertebrae.

WO2005/037137A2 discloses a spinal cage with a hollow interior receiving a bone graft. The spinal cage is integrally formed and can be easily implanted between two adjacent vertebrae.

Accordingly, the bone graft (including both organic and artificial bone) is accommodated in the interior of the prosthetic implant, interbody spinal fusion implant, spinal fusion implant assembly, or spinal cage. Bone proliferates along the interior of the prosthetic implant, interbody spinal fusion implant, spinal fusion implant assembly, or spinal cage and then covers the exterior thereof. The prosthetic implant, interbody spinal fusion implant, spinal fusion implant assembly, or spinal cage, however, is composed of metal or macromolecular material which provides poor bone guidance and bonding. New bone covers the exterior of the prosthetic implant, interbody spinal fusion implant, spinal fusion implant assembly, or spinal cage after fibered connective tissues are formed thereon. Thus, loose bone bonding with the prosthetic implant, interbody spinal fusion implant, spinal fusion implant assembly, or spinal cage and poor bone fusion are easily generated.

Hence, there is a need for a spinal fusion device receiving a bone graft. The spinal fusion device bears compression or stress from adjacent vertebrae and enables newgrown bone from the vertebrae to simultaneously grow along the interior and exterior of the spinal fusion device and fuse with the bone graft.

BRIEF SUMMARY OF THE INVENTION

Accordingly, an exemplary embodiment of the invention provides a spinal fusion device abutted and fixed between adjacent vertebrae. The spinal fusion device comprises a support frame comprising a plurality of extending bodies, each radially extending from a center of the support frame. A predetermined gap exists between every two adjacent extending bodies, receiving a bone graft.

The extending bodies are in the same horizontal plane.

The extending bodies have the same elevation.

The length of the extending bodies radially extending from the center of the support frame is the same.

The support frame further comprises a plurality of curved end portions respectively connected to the extending bodies.

The support frame further comprises an advance hole formed on one of the curved end portions.

The support frame further comprises a plurality of flat end portions respectively connected to the extending bodies.

The support frame further comprises an advance hole formed on one of the flat end portions.

The advance hole comprises inner threads.

The support frame further comprises a plurality of slip-proof protrusions formed on the surface thereof.

The support frame further comprises a central through hole formed in the center thereof.

The spinal fusion device further comprises at least one positioning member disposed in the support frame.

The positioning member comprises metal or a material through which X-rays cannot pass.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1A:
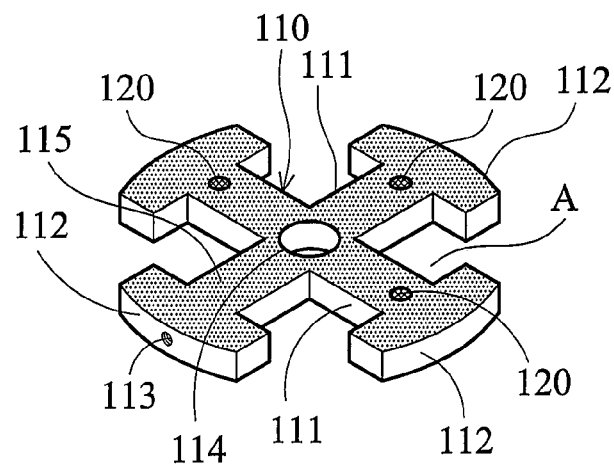
FIG. 1A is a schematic perspective view of a spinal fusion device of the invention.
Figure 1B:
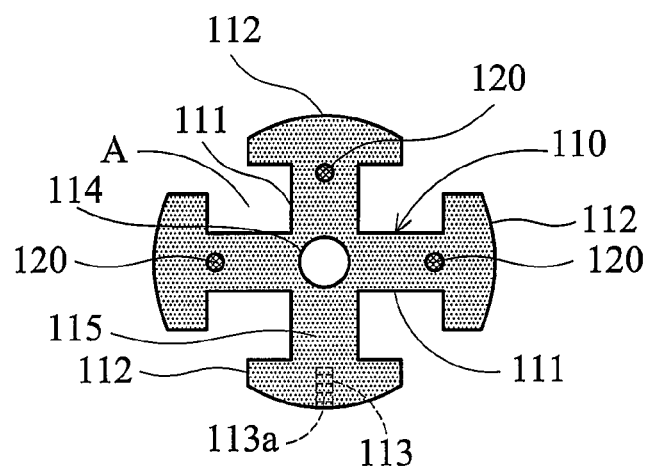
FIG. 1B is a schematic top view of FIG. 1A.

Referring to FIG. 1A and FIG. 1B, a spinal fusion device 100 abutting and fixed between two adjacent vertebrae comprises a support frame 110 and a plurality of positioning members 120. The support frame 110 comprises a plurality of extending bodies 111, a plurality of curved end portions 112, an advance hole 113, and a central through hole 114.

As shown in FIG. 1A and FIG. 1B, each of the extending bodies 111 radially and outwardly extends from a center of the support frame 110, and a predetermined gap A exists between two adjacent extending bodies 111. Moreover, the extending bodies 111 are in the same horizontal plane and have the same elevation. Specifically, the length of the extending bodies 111 radially extending from the center of the support frame 110 may be the same.

The curved end portions 112 are respectively connected to the extending bodies 111, and the advance hole 113 is formed on one of the curved end portions 112. Specifically, the advance hole 113 is formed on the edge or sidewall of one of the curved end portions 112. When the spinal fusion device 100 is implanted between two adjacent vertebrae, an implanting mechanism can be inserted into the advance hole 113, moving the spinal fusion device 100 to a suitable position between the vertebrae. Additionally, the advance hole 113 comprises inner threads 113a formed on the inner wall thereof, as shown in FIG. 1B. When inserted into the advance hole 113, the implanting mechanism can be fastened to the spinal fusion device 100, facilitating implantation thereof.

The central through hole 114 is formed in the center of the support frame 110, and the positioning members 120 are disposed in the support frame 110. Specifically, the positioning members 120 are respectively disposed in the extending bodies 111 of the support frame 110 and comprise metal or materials through which X-rays cannot pass. Accordingly, the positioning members 120 allow X-rays to detect the accurate position of the spinal fusion device 100 between the adjacent vertebrae.

Moreover, to enhance attachment between the spinal fusion device 100 and the vertebrae, the support frame 110 may have a coarse surface. Namely, the support frame 110 may comprise a plurality of small slip-proof protrusions 115 formed on the surface thereof, enhancing attachment between the spinal fusion device 100 (or support frame 110) and the vertebrae.

Figure 1C:
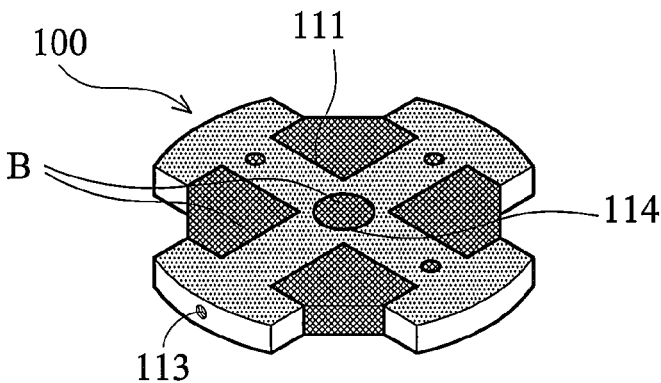
FIG. 1C is a schematic perspective view of the spinal fusion device of FIG. 1A combined with a bone graft.

Accordingly, before the spinal fusion device 100 is implanted in a gap between two adjacent vertebrae, a bone graft B (such as autologous tissue, allologous tissue, xenologous tissue or artificial bone) is filled in the central through hole 114 and predetermined gaps A between the extending bodies 111, as shown in FIG. 1C. After a disc between the adjacent vertebrae is removed, the spinal fusion device 100 with the bone graft B is implanted by the implanting mechanism in the gap vacated by the disc. Accordingly, the spinal fusion device 100 fixes the adjacent vertebrae and bears compression therefrom. Moreover, bone proliferated from the adjacent vertebrae fuses with the bone graft B along the interior and exterior of the spinal fusion device 100. Superior bone fusion is thus obtained.

Moreover, the autologous tissue may be selected from the group consisting of autologous bone, periosteum, marrow, blood, and stem cell. The xenologous tissue may be selected from the group consisting of human bone, periosteum, marrow, blood, and stem cell. The artificial bone may be selected from the group consisting of hydroxyapatite, tricalcium phosphate, biphasic ceramic, calcium sulfate, calcium carbonate, collagen, and gelation. Additionally, the aforementioned artificial bone has a porous structure, with an aperture density of 30% to 90% and aperture caliber of 100 μm to 1000 μm.

Figure 2A:
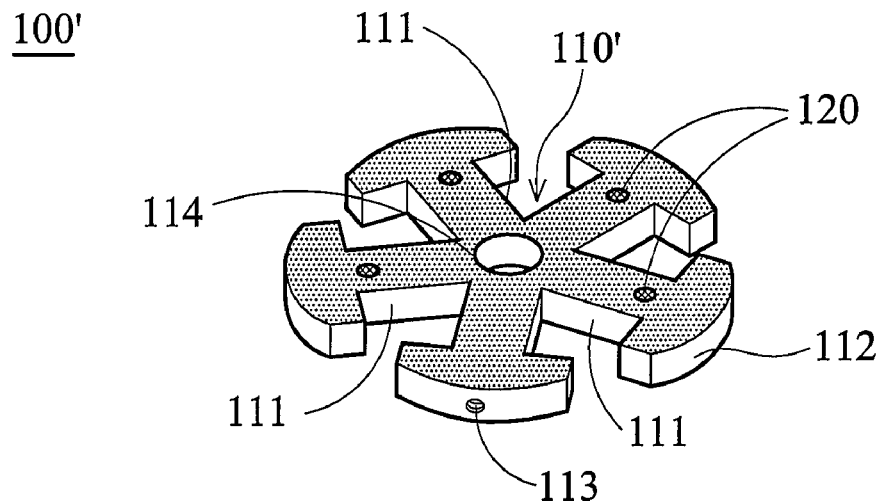
FIG. 2A is a schematic perspective view of another spinal fusion device of the invention.
Figure 2B:
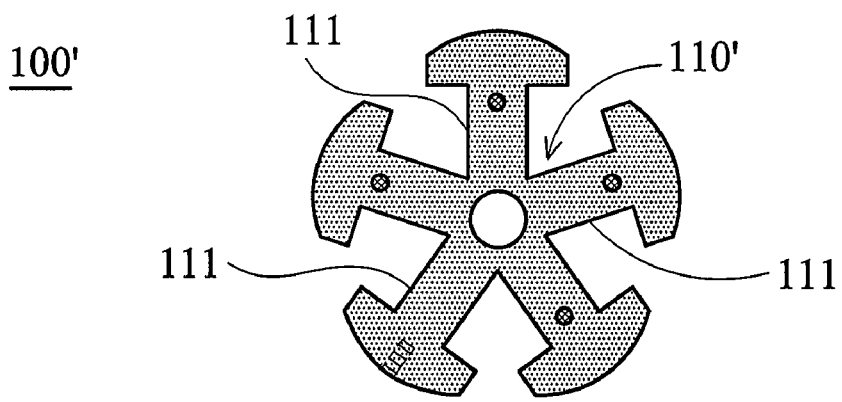
FIG. 2B is a schematic top view of FIG. 2A.

Moreover, the disclosed spinal fusion device is not limited to four extending bodies. Namely, the spinal fusion device may have more or less than four extending bodies as required. For example, as shown in FIG. 2A and FIG. 2B, a support frame 110' of a spinal fusion device 100' comprises five extending bodies 111. Structure, disposition, and function of other elements of the spinal fusion device 100' are the same as those of the spinal fusion device 100, and explanation thereof is omitted for simplicity.

More particularly, the disclosed spinal fusion device is not limited to the profiles shown in FIGS. 1A, 1B, 2A, and 2B. For example, the spinal fusion device may have the profile shown in FIG. 3A and FIG. 3B. Specifically, the major difference between a spinal fusion device 100" shown in FIG. 3A and FIG. 3B and the spinal fusion device 100 shown in FIG. 1A and FIG. 1B is that a support frame 110" of the spinal fusion device 100" comprises a plurality of curved extending bodies 111'. Structure, disposition, and function of other elements of the spinal fusion device 100" are the same as those of the spinal fusion device 100, and explanation thereof is omitted for simplicity. Additionally, a bone graft B can be filled in the central through hole 114 and predetermined gaps A' between the curved extending bodies 111', as shown in FIGS. 3A, 3B, and 3C.

Figure 3A:
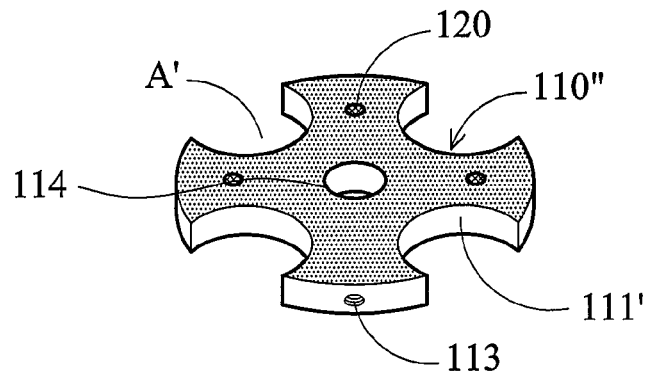
FIG. 3A is a schematic perspective view of yet another spinal fusion device of the invention.
Figure 3B:
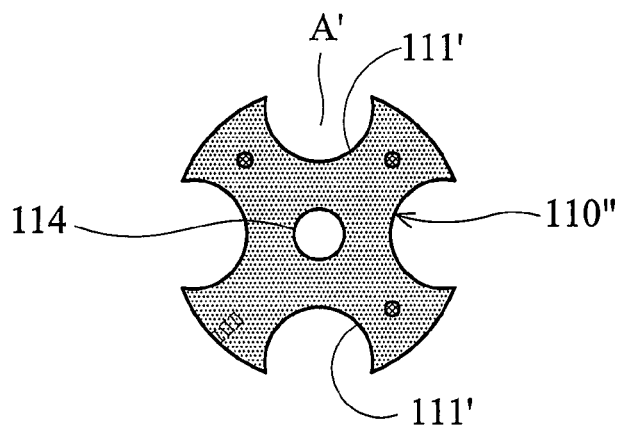
FIG. 3B is a schematic top view of FIG. 3A.
Figure 3C:
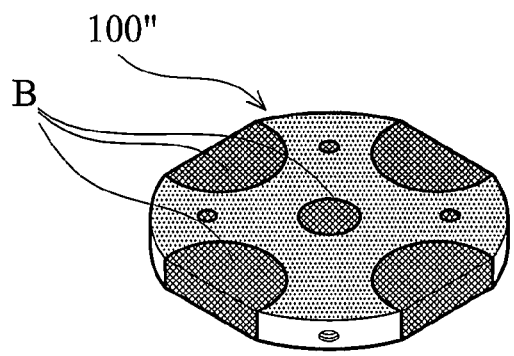
FIG. 3C is a schematic perspective view of the spinal fusion device of FIG. 3A combined with a bone graft.
Figure 4A:
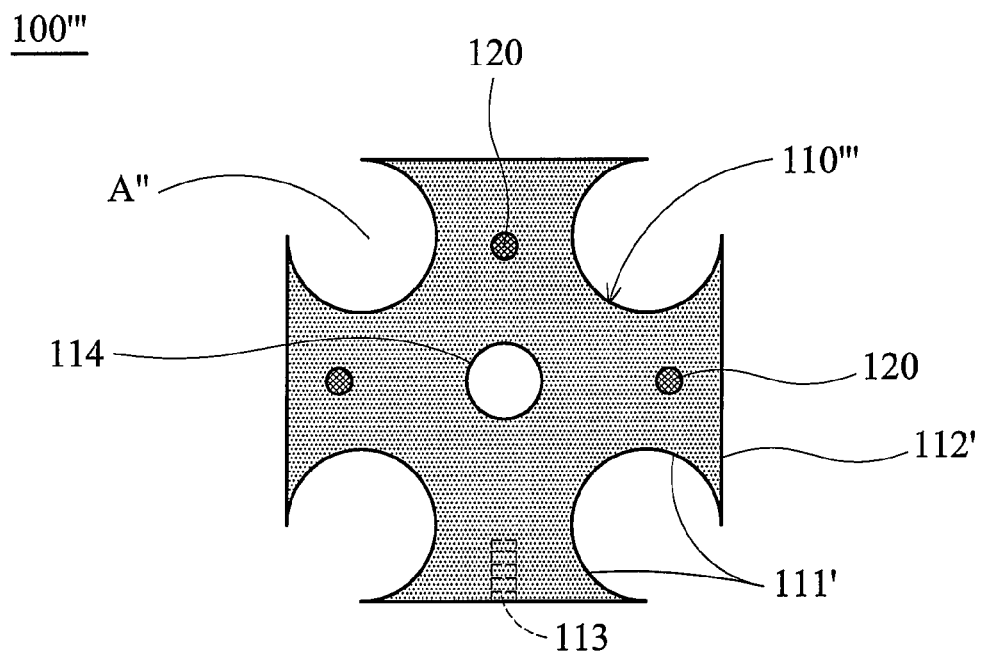
FIG. 4A is a schematic top view of still another spinal fusion device of the invention.
Figure 4B:
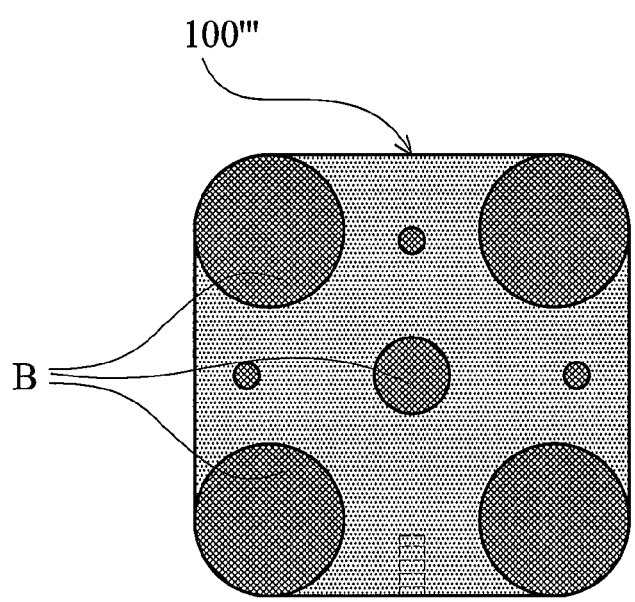
FIG. 4B is a schematic top view of the spinal fusion device of FIG. 4A combined with a bone graft.

Additionally, the disclosed spinal fusion device is not limited to the profiles shown in FIGS. 1A, 1B, 2A, 2B, 3A, and 3B. For example, the spinal fusion device may have the profile shown in FIG. 4A. Specifically, the major difference between a spinal fusion device 100'" shown in FIG. 4A and the spinal fusion device 100" shown in FIG. 3A and FIG. 3B is that a support frame 110'" of the spinal fusion device 100'" comprises a plurality of flat end portions 112'. Each flat end portion 112' is connected to each curved extending body 111', and the advance hole 113 is formed on one of the flat end portions 112'. Structure, disposition, and function of other elements of the spinal fusion device 100'" are the same as those of the spinal fusion device 100", and explanation thereof is omitted for simplicity. Similarly, a bone graft B can be filled in the central through hole 114 and predetermined gaps A" between the curved extending bodies 111', as shown in FIG. 4A and FIG. 4B.

Similarly, the disclosed spinal fusion device is not limited to four curved extending bodies. Namely, the spinal fusion device may have more or less than four curved extending bodies as required.

Moreover, the extending bodies of the disclosed spinal fusion devices may form a circular, oval or cone-like column.

In conclusion, in addition to enabling newgrown bone from the vertebrae to simultaneously grow along the interior and exterior of the spinal fusion devices and fuse with the bone graft, the disclosed spinal fusion devices provides excellent stability between two adjacent vertebrae.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A spinal fusion device for abutting and fixing between adjacent vertebrae, comprising:
a support frame comprising a plate extending in a horizontal plane, the plate having:
a central through hole,
a central portion surrounding the central through hole,
a plurality of flat extending bodies proportioned to fit into a gap between adjacent vertebrae vacated by a disc, and
a plurality of gaps respectively formed between adjacent extending bodies, wherein the plurality of gaps and the central through hole extend through the plate in a direction perpendicular to the horizontal plane,
wherein the extending bodies each comprise an arm portion and an end portion, the arm portion extending radially from the central portion in the horizontal plane and having a first end connected to the central portion and a second end opposite thereto, the end portion extending transversely to the arm portion in the horizontal plane, each end portion having a middle portion, a first protruding portion extending from the middle portion in a first direction, and a second protruding portion extending from the middle portion in a second direction opposite to the first, wherein the middle portion is connected to the second end of the arm portion, and
wherein each of the plurality of gaps is an open-ended recess completely separating the end and arm portions of two adjacent extending bodies; and
a bone graft filled into the central through hole and the plurality of gaps.

2. The spinal fusion device as claimed in claim 1, wherein the extending bodies are symmetrical with each other.

3. The spinal fusion device as claimed in claim 2, comprising at least four gaps.

4. The spinal fusion device as claimed in claim 1, wherein the length of the extending bodies radially extending from the center of the support frame is the same.

5. The spinal fusion device as claimed in claim 1, wherein the support frame further comprises an advance hole formed in one of the extending bodies.

6. The spinal fusion device as claimed in claim 5, wherein the advance hole comprises inner threads.

7. The spinal fusion device as claimed in claim 1, wherein each of the plurality of gaps is a semicircular cut-out formed in an outer perimeter of the plate.

8. The spinal fusion device as claimed in claim 7, wherein the support frame further comprises an advance hole formed in a surface of one end portion facing away from the central portion and extending toward the central portion in a direction parallel to the horizontal plane.

9. The spinal fusion device as claimed in claim 8, wherein the advance hole comprises inner threads.

10. The spinal fusion device as claimed in claim 1, wherein each arm portion has a rectangular profile in the horizontal plane, each corresponding end portion connected thereto comprises a flat inner surface facing towards the central portion, and the arm portion and corresponding end portion connect to form a "T" shape.

11. The spinal fusion device as claimed in claim 10, wherein the support frame further comprises an advance hole formed in an outer surface of one end portion facing away from the central portion and extending toward the central portion in a direction parallel to the horizontal plane.

12. The spinal fusion device as claimed in claim 11, wherein the advance hole comprises inner threads.

13. The spinal fusion device as claimed in claim 1, wherein the support frame further comprises a plurality of slip-proof protrusions formed on the surface thereof.

14. The spinal fusion device as claimed in claim 1, further comprising at least one positioning member disposed in the support frame.

15. The spinal fusion device as claimed in claim 14, wherein the positioning member comprises metal or a material through which X-rays cannot pass.

16. The spinal fusion device as claimed in claim 1, wherein the bone graft filled into the central through hole is separated from the bone graft filled into the gaps by the plate.

17. The spinal fusion device as claimed in claim 1, wherein the gaps are recesses into an outer edge of the plate.

18. A spinal fusion device comprising:
a support frame, for fixing between adjacent vertebrae of a spine having a superior-inferior axis, comprising:
a plurality of extending bodies, wherein each of the plurality of extending bodies comprises;
a central through hole,
a central portion surrounding the central through hole,
a plurality of extending bodies proportioned to fit into a gap between adjacent vertebrae vacated by a disc, and
a plurality of gaps respectively formed between adjacent extending bodies,
wherein the extending bodies each comprise an arm portion and an end portion, the arm portion extending radially from the central portion and having a first end connected to the central portion and a second end opposite thereto, each end portion extending transversely to the arm portion and having a middle portion, a first protruding portion extending from the middle portion in a first direction, and a second protruding portion extending from the middle portion in a second direction opposite to the first, wherein the middle portion is connected to the second end of the arm portion, and
wherein each of the plurality of extending bodies has an open end, and each of the plurality of gaps is a recess completely separating the open ends of two adjacent extending bodies; and
a bone graft filled into the central through hole and the plurality of gaps;
wherein an angle intersected between every two adjacent extending bodies is fixed at a predetermined value.

19. The spinal fusion device as claimed in claim 18, wherein the extending direction of the each of the plurality of extending bodies is perpendicular to the superior-inferior axis of the spine.

20. The spinal fusion device as claimed in claim 18, wherein the support frame and the plurality of extending bodies are integrally formed into a single piece.

21. The spinal fusion device as claimed in claim 18, wherein the predetermined value is ninety degrees.

22. The spinal fusion device as claimed in claim 18, wherein the predetermined value is sixty degrees.

23. The spinal fusion device as claimed in claim 18, wherein the bone graft filled into the central through hole is separated from the bone graft filled into the gaps.

24. The spinal fusion device as claimed in claim 18, wherein each of the plurality of gaps is a semicircular cut-out formed in an outer perimeter of the support frame.

25. The spinal fusion device as claimed in claim 18, wherein each arm portion has a rectangular profile, each corresponding end portion connected thereto comprises a flat inner surface facing towards the central portion, and the arm portion and corresponding end portion connect to form a "T" shape.

* * * * *